United States Patent
Schurr et al.

(10) Patent No.: US 9,603,614 B2
(45) Date of Patent: Mar. 28, 2017

(54) MEDICAL GRIPPING DEVICE

(75) Inventors: Marc O. Schurr, Tuebingen (DE); Chi-Nghia Ho, Stuttgart (DE); Andreas Kirschniak, Moenchengladbach (DE); Gunnar Anhoeck, Reutlingen (DE)

(73) Assignee: OVESCO ENDOSCOPY AG, Tuebingen (DE)

( * ) Notice: Subject to any disclaimer, the term of this patent is extended or adjusted under 35 U.S.C. 154(b) by 182 days.

(21) Appl. No.: 12/997,578

(22) PCT Filed: Jun. 10, 2009

(86) PCT No.: PCT/EP2009/057205
§ 371 (c)(1),
(2), (4) Date: Apr. 15, 2011

(87) PCT Pub. No.: WO2009/150184
PCT Pub. Date: Dec. 17, 2009

(65) Prior Publication Data
US 2011/0184458 A1    Jul. 28, 2011

(30) Foreign Application Priority Data

Jun. 11, 2008 (DE) .................... 20 2008 007 775 U

(51) Int. Cl.
*A61B 17/00* (2006.01)
*A61B 17/29* (2006.01)
*A61B 10/06* (2006.01)

(52) U.S. Cl.
CPC .............. *A61B 17/29* (2013.01); *A61B 10/06* (2013.01); *A61B 17/2909* (2013.01);
(Continued)

(58) Field of Classification Search
CPC ............ A61B 17/29; A61B 2017/2901; A61B 2017/2902; A61B 2017/2912;
(Continued)

(56) References Cited

U.S. PATENT DOCUMENTS

| 3,035,582 A | * | 5/1962 | Wright | ................... | A61B 90/50 269/45 |
| 4,326,530 A | | 4/1982 | Fleury, Jr. | | |
| 4,576,162 A | * | 3/1986 | McCorkle | .............. | A61B 17/29 294/100 |
| 4,686,965 A | * | 8/1987 | Bonnet | .............. | A61B 17/0218 600/104 |

(Continued)

FOREIGN PATENT DOCUMENTS

DE    44 20 284 A1    12/1995
JP    07-194601       8/1995

OTHER PUBLICATIONS

Japanese Office Action in JP Application No. 2011-512979, dated Apr. 30, 2013.
(Continued)

*Primary Examiner* — Amy R Weisberg
(74) *Attorney, Agent, or Firm* — TechLaw LLP

(57) ABSTRACT

The present invention relates to an endoscope cap with a holding and withdrawal device for a tissue clip (4) that can be placed onto a spreading sleeve (3) of the endoscope cap (1). The endoscope cap comprises an end groove (7) that opens at the front edge of the spreading sleeve (3) and that slits open the cap wall on both sides, and a withdrawal thread or web (11) that radially traverses the end groove (7) in a forward axial cap section and that is introduced or can be introduced slideably into an endoscope channel for actuation thereof at a radial inside of the endoscope cap (1).

6 Claims, 9 Drawing Sheets

(52) U.S. Cl.
CPC .............. *A61B 2017/00278* (2013.01); *A61B 2017/00398* (2013.01); *A61B 2017/00455* (2013.01); *A61B 2017/2902* (2013.01); *A61B 2017/294* (2013.01); *A61B 2017/2905* (2013.01); *A61B 2017/2911* (2013.01); *A61B 2017/2924* (2013.01); *A61B 2017/2927* (2013.01); *A61B 2017/2932* (2013.01); *A61B 2017/2933* (2013.01); *A61B 2017/2938* (2013.01); *A61B 2017/2939* (2013.01)

(58) Field of Classification Search
CPC ...... A61B 2017/2938; A61B 2017/294; A61B 2017/2941; A61B 2017/2906
USPC ....... 606/205–210, 167, 170, 141, 148, 150; 600/104; 81/345–351; 128/897–899; 294/87.1
See application file for complete search history.

(56) References Cited

U.S. PATENT DOCUMENTS

| | | | | |
|---|---|---|---|---|
| 4,909,789 A * | 3/1990 | Taguchi | A61B 17/0218 | 604/107 |
| 5,158,561 A * | 10/1992 | Rydell et al. | | 606/113 |
| 5,195,506 A * | 3/1993 | Hulfish | A61B 17/0218 | 600/204 |
| 5,228,451 A * | 7/1993 | Bales | A61B 10/06 | 600/564 |
| 5,312,391 A * | 5/1994 | Wilk | A61B 17/00234 | 604/264 |
| 5,391,180 A * | 2/1995 | Tovey | A61B 1/32 | 600/224 |
| 5,403,332 A * | 4/1995 | Christoudias | A61B 17/29 | 294/115 |
| 5,439,478 A * | 8/1995 | Palmer | A61B 1/00087 | 600/564 |
| 5,441,494 A * | 8/1995 | Ortiz | | 606/1 |
| 5,474,057 A * | 12/1995 | Makower | A61B 17/0218 | 600/205 |
| 5,490,819 A * | 2/1996 | Nicholas | A61B 1/32 | 600/201 |
| 5,511,564 A * | 4/1996 | Wilk | A61B 17/00234 | 128/898 |
| 5,514,157 A * | 5/1996 | Nicholas | A61B 17/0218 | 600/201 |
| 5,599,151 A * | 2/1997 | Daum | B25J 3/00 | 294/111 |
| 5,716,374 A * | 2/1998 | Francese | A61B 10/06 | 600/564 |
| 5,722,421 A * | 3/1998 | Francese | A61B 10/06 | 600/564 |
| 5,792,165 A | 8/1998 | Klieman | | |
| 5,810,876 A * | 9/1998 | Kelleher | A61B 10/06 | 606/170 |
| 5,820,630 A * | 10/1998 | Lind | A61B 10/06 | 606/205 |
| 5,840,044 A * | 11/1998 | Dassa | A61B 10/0266 | 600/567 |
| 5,895,361 A * | 4/1999 | Turturro | A61B 10/06 | 30/124 |
| 5,908,437 A * | 6/1999 | Asano | A61B 10/06 | 606/167 |
| 5,954,731 A * | 9/1999 | Yoon | A61B 17/062 | 606/139 |
| 5,984,932 A * | 11/1999 | Yoon | A61B 17/0469 | 606/147 |
| 5,993,461 A * | 11/1999 | Abae | A61B 17/4241 | 606/119 |
| 5,993,466 A * | 11/1999 | Yoon | A61B 17/062 | 606/144 |
| 6,066,102 A * | 5/2000 | Townsend | A61B 10/06 | 600/104 |
| 6,074,408 A * | 6/2000 | Freeman | A61B 17/29 | 606/205 |
| 6,162,239 A * | 12/2000 | Manhes | A61B 17/29 | 606/205 |
| 6,264,617 B1 * | 7/2001 | Bales | A61B 10/06 | 600/564 |
| 6,299,630 B1 * | 10/2001 | Yamamoto | A61B 1/018 | 606/170 |
| 6,309,404 B1 * | 10/2001 | Krzyzanowski | A61B 10/06 | 606/205 |
| 6,409,678 B1 * | 6/2002 | Ouchi | A61B 10/00 | 600/532 |
| 6,508,827 B1 * | 1/2003 | Manhes | A61B 17/29 | 600/104 |
| 6,673,092 B1 | 1/2004 | Bacher | | |
| 6,821,285 B2 * | 11/2004 | Laufer et al. | | 606/153 |
| 7,682,372 B2 * | 3/2010 | Peterson | A61B 17/04 | 606/211 |
| 7,867,228 B2 * | 1/2011 | Nobis | A61B 17/320016 | 606/45 |
| 8,182,495 B2 * | 5/2012 | DiStefano | A61B 17/04 | 606/139 |
| 9,089,393 B2 * | 7/2015 | Khamis | A61F 2/0045 | |
| 2001/0047124 A1 * | 11/2001 | Yamamoto | A61B 10/06 | 600/101 |
| 2002/0017515 A1 * | 2/2002 | Obata | A61B 1/0011 | 219/137 R |
| 2002/0120277 A1 * | 8/2002 | Hauschild | A61B 17/221 | 606/108 |
| 2002/0165580 A1 * | 11/2002 | Zwiefel | A61B 10/06 | 606/205 |
| 2003/0109898 A1 * | 6/2003 | Schwarz et al. | | 606/205 |
| 2004/0260198 A1 * | 12/2004 | Rothberg | A61B 10/06 | 600/564 |
| 2005/0043758 A1 * | 2/2005 | Golden | A61B 10/06 | 606/206 |
| 2005/0049520 A1 * | 3/2005 | Nakao | A61B 10/06 | 600/562 |
| 2005/0124912 A1 * | 6/2005 | Griego | A61B 10/04 | 600/564 |
| 2005/0261735 A1 * | 11/2005 | Shibata | A61B 10/06 | 606/205 |
| 2006/0184198 A1 * | 8/2006 | Bales | A61B 10/06 | 606/205 |
| 2007/0244511 A1 * | 10/2007 | Weizman | A61B 10/06 | 606/205 |
| 2007/0244512 A1 * | 10/2007 | Measamer | A61B 10/06 | 606/205 |
| 2007/0244513 A1 * | 10/2007 | Weizman | A61B 10/06 | 606/205 |
| 2007/0244514 A1 * | 10/2007 | Weizman | A61B 10/06 | 606/205 |
| 2007/0276430 A1 | 11/2007 | Lee | | |
| 2007/0299387 A1 * | 12/2007 | Williams | A61B 1/00052 | 604/22 |
| 2008/0119880 A1 * | 5/2008 | Chu | A61B 17/29 | 606/157 |
| 2008/0154300 A1 * | 6/2008 | Jabbour | A61B 17/2812 | 606/205 |
| 2009/0105534 A1 * | 4/2009 | Nakagawa | A61B 1/00137 | 600/106 |
| 2014/0378998 A1 * | 12/2014 | Rizzuto | A61B 17/29 | 606/130 |
| 2016/0192959 A1 * | 7/2016 | Danieli | A61B 17/29 | 606/208 |

OTHER PUBLICATIONS

European Office Action in EP Application No. 09 761 747.6, dated Nov. 27, 2012.

* cited by examiner

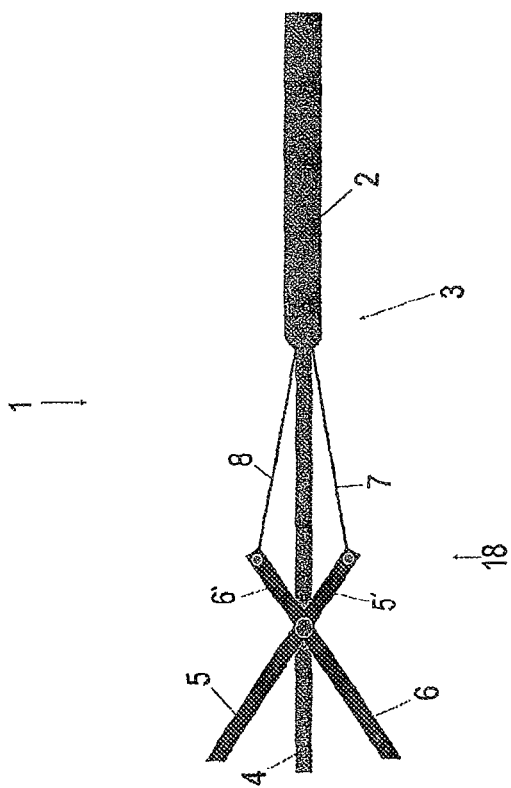

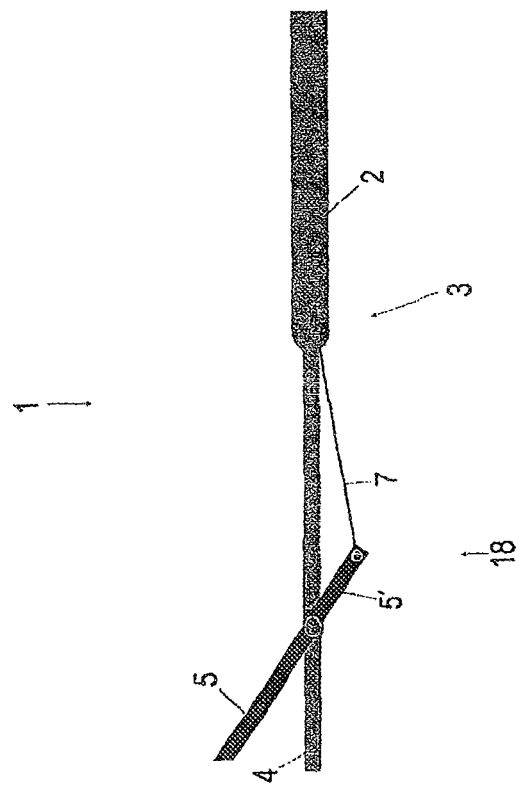

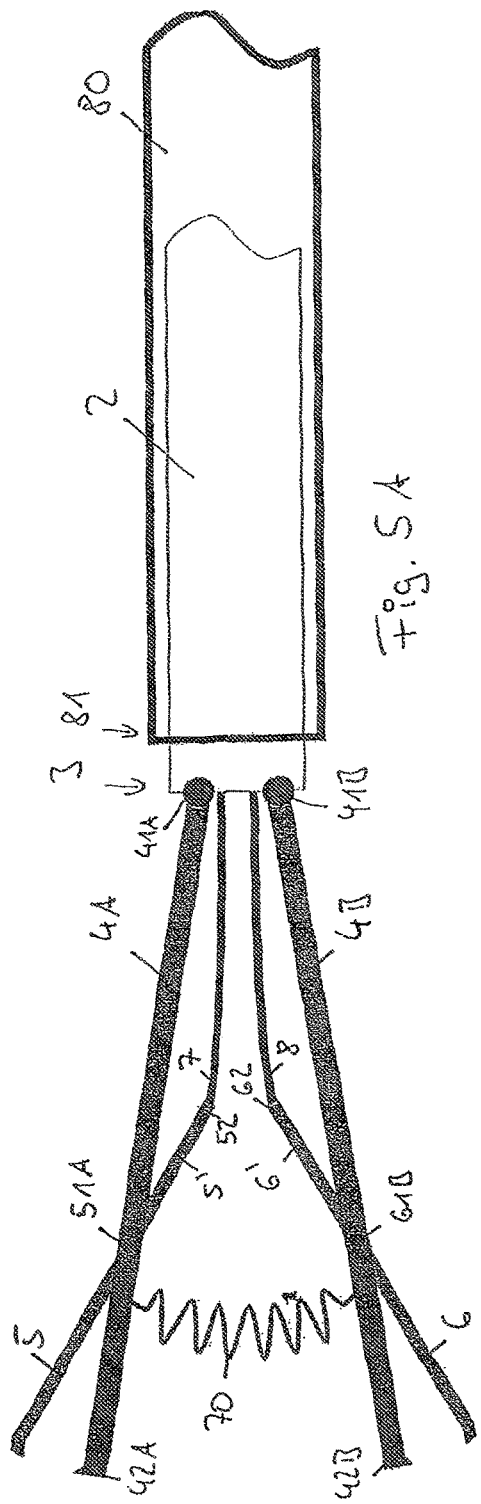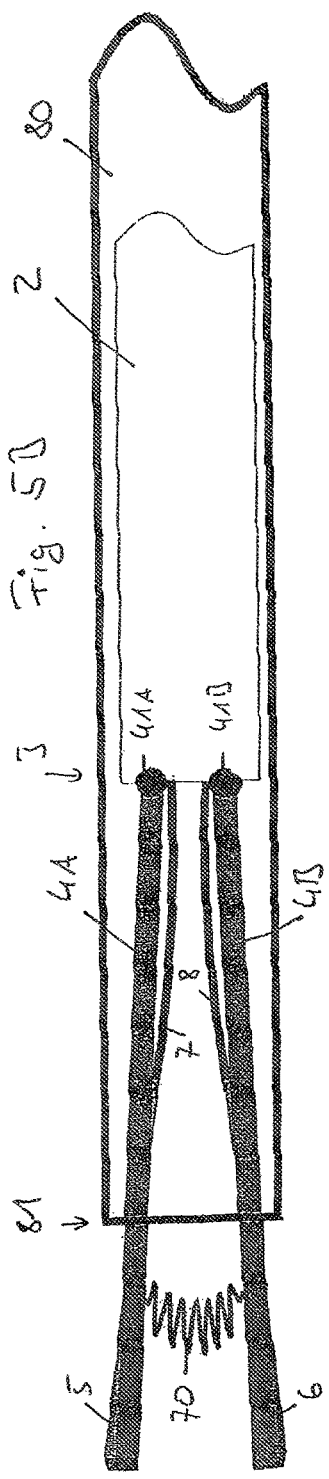

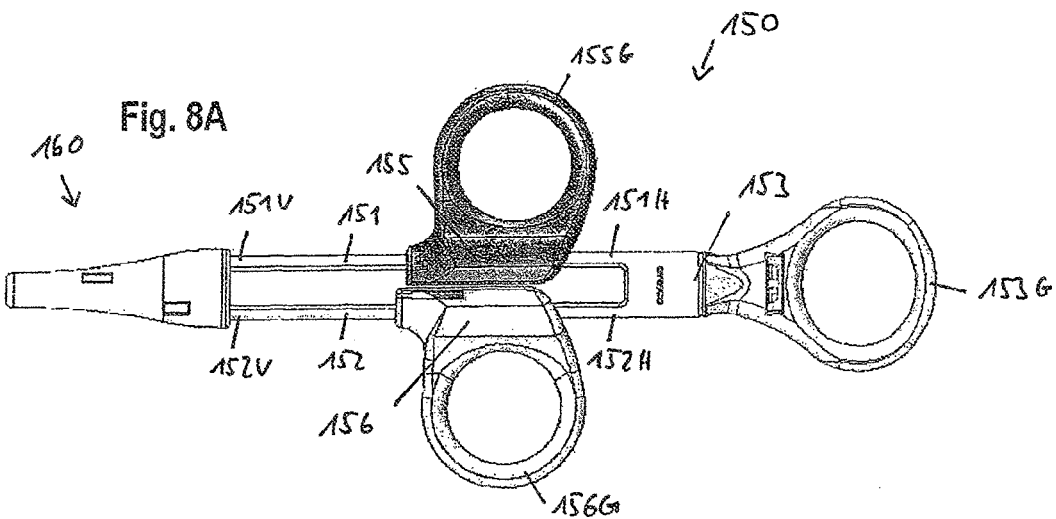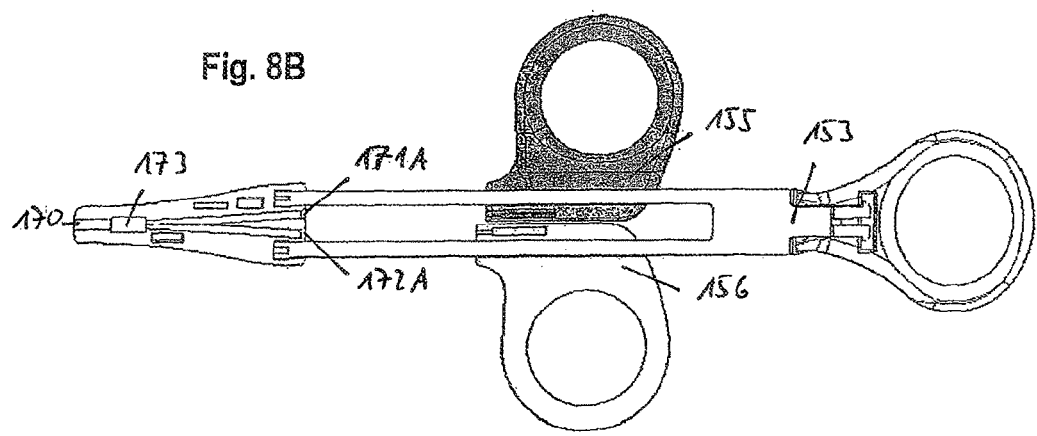

MEDICAL GRIPPING DEVICE

TECHNICAL FIELD

The present invention relates to a medical gripping device and especially to a medical gripping device including plural branches that are individually controllable.

STATE OF THE ART

Today the use of flexible endoscopy is common standard for the diagnostic and therapeutic treatment of diseases of the gastro-intestinal tract. A flexible endoscope is inserted into natural orifices of the body such as the mouth and the anus. Since with this surgery, no direct intervention into the tissue or the like to be operated is possible, flexible endoscopic instruments have to be employed. Also gripping instruments are used which, for instance, can take tissue samples or by which tissue can be gripped and manipulated.

In the state of the art a gripping device is known which has a hollow flexible shaft at the front end of which two branches are rotatably mounted. The two branches form a type of mouth which can open to the front end of the gripping device. At the rear end of each branch a high-tensile and compression-proof rope is mounted via a lever arm. The two ropes are connected to one end of a Bowden cable extending through the hollow shaft and being connected to a handle at its other end. Upon actuating the handle the mouth provided at the other end of the gripping device can be opened and closed. The entire gripping device is inserted into the body through a working channel of an endoscope.

In accordance with another instrument known from the state of the art, a gripping device has a flexible shaft including a rigid web (or a rigid mouth part) at one end. At such rigid web a branch is hinged which is movable by means of a Bowden cable. The Bowden cable extends in the flexible shaft and is connected to a grip at the other end of the gripping device. Upon actuating the grip the branch is opened and closed. This gripping device can be inserted through a working channel of an endoscope.

The gripping devices of the state of the art exhibit several drawbacks, however. In practice it is frequently necessary to interconnect tissue parts or to close openings in the tissue. In this context, it is necessary that the respective tissue parts or the opposed marginal portions of the openings can be gripped and thus fixed. Otherwise no controlled connection or no controlled closure of the tissue is possible. If, for instance, a perforation cannot be closed, an open surgical intervention frequently has to be carried out in order to avoid complications caused by penetrating germs. Since, however, the gripping devices of the state of the art have only one mouth each, it is absolutely necessary that at least two of such gripping devices are used. This is difficult, however, with respect to the (second access) second working channel required in such case in the endoscope or an additional second endoscope due to the constriction of the natural body orifices such as e.g. esophagus, small and large intestines. Recently, research has been done with novel surgery techniques, the so called NOTES (Natural Orifice Transluminal Endoscopic Surgery) in which it is attempted to get into body cavities such as the abdominal cavity without a skin incision so as to operate there. The accesses are provided with the aid of the flexible instrument through the stomach, large intestine or vagina, for instance. These accesses have to be effectively closed after surgery. This is only possible, however, when the respective marginal portions can be gripped and thus fixed.

SUMMARY OF THE INVENTION

Therefore it is an object of the invention to provide a medical gripping device by which at least two tissue parts can be separately gripped and thus fixed. It is another object of the invention to provide a handle for such medical gripping device by which the medical gripping device can be held and actuated. Another object of the present invention consists in providing a connecting element between the medical gripping device and the handle by which individual operations independent of each other of the individual branches can be realized.

The object of the present invention is achieved by a medical gripping device according to claim 1. Further advantageous developments of the medical gripping device are the subject matter of the subclaims.

In accordance with a first aspect of the present invention, a medical gripping device comprises a flexible shaft having a front end and a rear end, a web consisting of at least one web element mounted to the front end of the shaft, at least two branches hinged to the web and at least two flexible control mechanisms arranged at least partly in the shaft. Moreover, at the rear end of the flexible shaft a handle is provided by which the medical gripping device can be held and actuated.

The flexible control mechanisms can be configured as Bowden cables each comprising a flexible cable shiftably fed within its own (internal) flexible cable jacket. Both cable jackets of the Bowden cables are then installed within a common through passage of the shaft, so that the flexible cables are capable to transmit both push- and pull forces.

In this medical gripping device each individual branch is movable vis-à-vis the web by means of a separate control mechanism. That is to say the gripping device includes at least two mouths adapted to be opened and closed independently of each other. Thus at least two tissue portions can be separately gripped and fixed. The shaft of the gripping device is flexible so that it produces as small restoring forces as possible when it is deformed from its initial shape. At the front end of the shaft also a small projection can be provided to which the web and the branches can be mounted. The branches can have barbs or teeth, for instance, they can be profiled or flat, straight or curved. The web elements can be appropriately formed such that they prevent the gripped tissue from slipping out of the respective mouth in interaction with the branches. The branches and web elements can especially be formed such that they do not injure the gripped tissue. At the rear end of the flexible shaft a handle is provided. This handle permits to precisely hold and guide the medical gripping device and simultaneously to precisely actuate the branches. The handle can be disposed either directly at the rear end of the flexible shaft or an adaptor can be provided there between, as will be described hereinafter.

In accordance with a further development of the medical gripping device, a connecting element is provided between the rear end of the flexible shaft and the front end of the handle, the connecting element having a through passage toward the flexible shaft in which through passage all transmission elements of the control devices are jointly guided. The through passage in the connecting element is then branched so that toward the handle a respective through passage is provided for each transmission element.

Such connecting element has the advantage that the transmission elements designed as components exhibiting tensile and shearing rigidity can be actuated individually without exerting such a strong mutually influence that an individual and precise control is impaired or prevented. More precisely, it may happen that when no connecting element is provided and the transmission elements are inserted directly in the one through hole of the flexible shaft, high friction is prevailing between the transmission elements and thus an operation of the one transmission element causes a movement of the other one. The risk of mutual influence is especially high in the area of combining or inserting the transmission elements, as the transmission elements are slightly bent due to the design and can be forced against each other. Moreover, lubrication is impeded in this area compared to the flexible shaft. Such a connecting element can also reduce the friction of the transmission elements vis-à-vis the surrounding wall by adapting the material and the geometry to the surrounding wall.

In accordance with a development of the medical gripping device, at the branching of the through passage to the through passages a chamber is provided for facilitating the branching or combining of the transmission elements.

Such a chamber is arranged at a position where the transmission elements have the largest bending or curvature within the connecting element. The transmission elements are inserted at the rear end of the connecting element in through passages which extend substantially straight in longitudinal direction of the connecting element. Nevertheless these through passages extend in radial direction toward the front end and finally unite to form one single through passage which extends along the central axis of the connecting element. Therefore, each individual through passage has a certain kink from the rear end to the front end of the connecting element. Moreover at this position the transmission elements are combined. Due to the afore-described behavior of the transmission elements during operation of the branches it is especially probable in this area that the transmission elements mutually influence each other. The chamber permits a certain evading movement of the transmission elements in the combining area and thus enhances the precision when operating the branches.

According to a further development of the medical gripping device, the openings of the through passages toward the handle are located in a plane perpendicular to the axis of the connecting element on an orbit.

In this way all through passages are inclined in the area of the rear end of the connecting element at the same angle vis-à-vis the through passage at the front end so that the transmission elements are not different regarding their friction in the through passage.

According to a further development of the medical gripping device, the openings of the through passages toward the handle are evenly spaced on the orbit.

In this manner, the through passages are arranged rotation-symmetrically about the axis of the connecting element and thus of the flexible shaft. Since the position of the through passage corresponds to the position of the pertinent operating element, this further development permits the optimum distribution of a plurality of operating elements or control devices around the axis of the gripping device.

In accordance with a further development of the medical gripping device, the openings of the through passages are widened toward the handle.

Such widening of the through passages permits smoother insertion of the transmission elements into the through holes and prevents a transmission element from getting stuck in the area of the opening edge. This is interesting especially when the transmission element is in the form of a resilient spiral exhibiting shearing and tensile strength. In this case a sharp opening edge of the through hole could get hooked between two neighboring windings of the spiral. Thus also small positioning inaccuracies between the through hole and the operating element can be compensated.

In accordance with a further development of the medical gripping device, the handle includes two rails extending substantially in parallel to the axis of the flexible shaft from the rear end thereof. At each rail a slide is provided which is movable along the corresponding rail. Each slide is connected to the pertinent control mechanism with shearing and tensile strength so that a movement of each slide along the respective rail is transmitted by a pertinent transmission element of the control mechanisms to the respective branch.

This represents an especially advantageous embodiment of operating elements. The user can simultaneously grip the slide with his/her hand and thus effectuate a precise simultaneous control of all branches. Moreover, the use of slides running on rails is very intuitive for the user. The branches can be controlled, other than by a pushing movement along the axis of the gripping device, also by rotating movements of e.g. buttons or rings attached to the handle. In this way the user can more easily confuse the opening and closing directions of the branches. With the design suggested here, on the other hand, such confusions are practically excluded in the first place.

According to a further development of the medical gripping device, a gripping element is provided at each slide.

In order to facilitate for the user to simultaneously hold, guide and precisely control the gripping device, gripping elements are provided from the slides which can be gripped especially easily.

In accordance with a further development of the medical gripping device, the rails are interconnected at their end distant from the body and another gripping element is provided at this connecting portion.

In this way it is easier for the user to safely guide the gripping device.

According to a further development of the medical gripping device, the further gripping element is offset and/or inclined vis-à-vis the central axis of the rails so as to permit an ergonomic hand posture of a gripping person.

The arrangement of the gripping elements is not fixed a priori but can be adapted to the ergonomics of the user. It has to be taken into consideration in this context, for example, whether the user of the gripping device is positioned more behind or more above the device. Accordingly, a convenient hand posture is varied at the handle of the gripping device.

In accordance with a further development of the medical gripping device, the gripping elements are formed by eyes whose through holes have central axes in parallel to each other.

Such eyes constitute a particularly advantageous embodiment for the gripping elements. The user can easily push a finger through each eye, thereby obtaining a safe grip and a good tactile feedback from the gripping device. Eyes are especially suited as gripping elements, because the hand or the finger can be effectively prevented from slipping off. These eyes need not necessarily be circular. In order to permit an as flat design of the handle as possible the eyes are arranged in this embodiment such that all of their central axes are in parallel to one another. In order to permit an ergonomic hand posture it is also possible to rotate one or more eyes. However, this enlarges the overall thickness of the handle. It is a space-saving alternative hereto to impart, e.g., a slightly oval shape to the eye and otherwise to maintain the central axes of the eyes in parallel.

According to a further development of the medical gripping device, each slide encompasses the pertinent rail so that the slide is prevented from releasing from the rail.

In this way, a slide is safely prevented from releasing from the pertinent rail. It is also possible, however, to mount the slide on the rail with the aid of a snap or click fit so that no tool and/or mounting material is required for attaching the slide.

According to a further development of the medical gripping device, the transmission element of each control mechanism is connected to the respective slide between the two rails.

In this way, the transmission elements are arranged in the area of the handle as closely as possible to the central axis of the gripping device so that the curvature of the through passages in the connecting element can be as small as possible.

According to a further development of the medical gripping device, the rails are shaped such that rotation of the pertinent slide about the respective rail is prevented.

That is to say, the rails have a non-circular cross-section. In this way it is reliably prevented that the gripping elements back away when the user grips them and that the use of the gripping device is thus impeded. In addition, the slide and the rail are positive-locking in circumferential direction of the rail, wherein a certain play is provided between them so as to ensure displacing of the slide along the rail.

In accordance with a further development of the medical gripping device, each slide is adapted to be fixed on the pertinent rail so that the operating position of the pertinent branch is fixed.

In this way the fixing can be brought about by a suitable selection of the friction coefficient between the rail and the slide, for instance by appropriate selection of the material or the surface design. As an alternative, also a type of locking brake can be provided as fixing means. This alternative would have the advantage that the friction of the entire control means can be kept as low as possible so that the user gets a particularly good feedback from the branches.

According to a further development of the medical gripping device, the transmission elements are detachably mounted at the slides by means of undercuts.

This is an embodiment which makes the use of additional mounting means redundant. Thus the transmission elements can be mounted quickly and safely to the slide without using any tools.

Altogether the handle can be configured so that it can be assembled by simple plug-in and click fits without any tools being required. Preferably the individual parts are made of plastic material by e.g. injection molding.

According to a further development of the medical gripping device, the web is hinged to the front end of the shaft. In this way the web can be pivoted vis-à-vis the shaft.

This is advantageous when tissue is to be gripped at a position where there is very little space or when the normal to the plane formed by the tissue edges to be gripped does not coincide with the longitudinal axis of the shaft. That is to say, the mouths can be inclined in their entirety vis-à-vis the shaft so that an even more unrestricted control of the medical gripping device is ensured.

According to a further embodiment of the medical gripping device, a separate control mechanism is provided for pivoting the web vis-à-vis the shaft.

This control mechanism can be one of the control mechanisms shown here, wherein an additional operating element can be provided at the handle for pivoting the web. Pivoting the web vis-à-vis the shaft can be possible in one or more directions. For pivoting to more directions possibly plural control mechanisms may be required.

All features and characteristics shown here can be employed in any combination. Especially different embodiments of the branches (with/without cutting edges, straight or curved, . . . ) webs (one web element, divided web, spring/elastic element between web elements, . . . ) and control mechanisms (electric/mechanical control mechanism, automatically opening/closing, . . . ) can be combined with different handles and/or transmission elements (electric wires, Bowden cables, combinations thereof).

Hereinafter the structure of the actual gripping device is described in detail.

The web of the medical gripping device consists of at least two web elements, with maximally one of the web elements being rigidly mounted to the shaft and the other web elements being rotatably hinged to the front end of the shaft or the maximally one rigid web element. That is to say, either all of the web elements are rotatably hinged to the front end of the shaft or one web element is rigidly connected to the front end of the shaft and the other web elements are rotatably hinged to the front end of the shaft or to the one rigid web element. Between or at the web elements at least one element is arranged such that the movable web elements can be moved at least in one direction by means of said element. Moreover, each branch of the gripping device is rotatably hinged to a web element.

Further, at least one elastic element can be arranged at the web elements such that it forces the web elements apart at their end distant from the body. Either an elastic element can be provided which forces all web elements apart or plural elastic elements can be provided which force apart two web elements at a time. The at least one elastic element can be arranged, for instance, in the respective mouth between the web elements and can force the web elements apart. This is possible, for instance, by compression springs or rubber members. In contrast to that, the at least one elastic element can also be arranged outside the mouths and can pull the web elements apart. This can be realized, for example, by a curved extension spring. Instead of an elastic element, also a magnetic element can do this job, wherein the magnetic element can be contained in the web elements. In addition, also a different element such as a type of microscopic air pressure spring could be employed. These elements can be alternatively arranged also between the web elements and the shaft of the gripping device.

As an alternative to the afore-described structure, electric micro-motors, for instance, may regulate the distance between the web elements in the future. This embodiment may be employed in the near future already due to the rapid development in this field.

The web elements can also have a completely different design. For instance, the individually movable web elements can be made of an elastic material such as spring steel, for example. These web elements are then connected at the end facing the shaft such that the ends of the web elements opposed to these connected ends move apart from each other by their inherent elasticity.

This configuration is especially reasonable when the medical gripping device according to the invention is used in combination with an endoscope. In this case the gripping device according to the invention is inserted through a working channel of the endoscope. The web elements whose front ends strive in any one of the afore-described ways for moving away from each other can do so unrestrictedly as long as the entire head of the gripping device according to the invention consisting of the branches and the web elements protrudes from the working channel of the endoscope. If, however, the head of the gripping device is pulled somewhat into a sleeve provided at the end of the endoscope, the web elements are adjacent to the sleeve and are deformed toward the axis of the gripping device when the gripping device is pulled further into the sleeve. It is also possible to move or slip on the sleeve. What is solely important is the movement of the gripping device relative to the sleeve. When the head of the gripping device is completely pushed out of the sleeve again, the front ends of the web elements move apart from each other again. In this manner, the distance of the front ends of the web elements and thus of the inner edges of the mouths from each other can be adjusted. The distance of the web elements can thus be adapted to the distance of the tissue portions to be gripped. The sleeve can also be part of an endoscope.

In the medical gripping device each of the control mechanisms includes a transmission element exhibiting tensile and compressive strength. The at least two transmission elements jointly extend in the shaft, each of these transmission elements being connected to a branch at the front end of the shaft. Moreover, each of the control mechanisms includes a control device provided at the rear end of the shaft and connected to the pertinent transmission element. Each transmission element transmits the movement output by the respective control device to the respective branch. The transmission of the movement also includes a transmission of movement signals which are then converted to movements in the head of the gripping device, for instance. The signals may be electric signals which are transmitted by electric wires. As a further alternative, the branches can also be automatically opened by means of magnets, elastic elements or the like, and instead of the transmission element exhibiting tensile and compressive strength a transmission element exhibiting tensile strength only is provided. Then the opening operation of the mouths takes place automatically and the closing operation is carried out by the transmission elements. The advantage is that transmission elements which need not exhibit compressive strength require a smaller cross-sectional area. In this case it should be ensured, however, that the mouths do not open again accidentally when the gripping device of the respective transmission element, for instance, is accidentally released. Hereinafter possible gripping elements and the alternatives thereto will be described in detail.

The branches and/or the pertinent web elements of the medical gripping device can also be distinguishable. Furthermore, the pertinent control devices can be distinguishable, wherein a definite association of the respective branch with the pertinent control device is possible. In this way, prior to operating a control device it is certain which branch is actuated. In addition, it can be safely decided in this manner which control device is to be actuated in order to open a particular mouth. An operation of the wrong branch can result in the fact that an already gripped tissue portion gets lost and thus the total period of surgery is considerably prolonged. The consequence can also be, for instance, that the marginal portions fray due to the frequent manipulation so that the opening cannot be safely closed any more. In this case, frequently an open surgical intervention including all its detrimental consequences has to be carried out.

Especially the branches and/or web elements are distinguishable by their color, their shape and/or their material. For instance, symbols or grooves can be formed at the branches and/or the web elements which are appropriately found again at the corresponding control devices. Also engravings can be provided. Colors are suited for distinction only when the branches and/or web elements can be viewed by a color camera. The material can be used for distinction when it has a different surface nature, for instance, such as different roughness, different reflection or different color. A different transparency of the material can also be used for distinction. It is probable that in the future more plastic materials will be employed for medical purposes. They can possibly be transparent.

In the medical gripping device the branches and/or the web elements can exhibit cutting edges. By these cutting edges for instance tissue parts can be separated or a seam can be ripped.

Advantageously the branches and the web elements are arranged symmetrically and the branches are rotatable in radial direction with respect to the axis of the gripping device. That means that the branches and the web elements are equally spaced in the circumferential direction of the gripping device.

The web elements can also be rotatable in radial direction with respect to the axis of the gripping device. Alternatively, the branches can move in tangential direction to the axis of the gripping device or in another direction to the same.

The web and the branches usually have an equal length toward their front end. They can also be configured such that the web, for instance, projects further forward than the branches, however. Also, the individual web elements and the individual branches can have different lengths. Advantageous effects of the invention:

BRIEF DESCRIPTION OF THE FIGURES OF THE DRAWINGS

These and further objects, features and advantages of the present invention are evident from the embodiments described hereinafter in detail with reference to the enclosed figures.

FIG. 1 is a lateral view of a head of a medical gripping device according to a first embodiment of the present invention in which both mouths are opened.

FIG. 2 is a lateral view of the head of the medical gripping device according to the first embodiment in which one mouth is opened.

FIGS. 5A and 5B are lateral views of a medical gripping device according to a second embodiment of the present invention, wherein in FIG. 5A the mouths are opened and the web elements are spaced apart from each other and in FIG. 5B the mouths are closed and the web elements are compressed.

FIG. 8 is a lateral view of the handle.

WAYS OF REALIZING THE INVENTION

First Embodiment

Figure 3A:
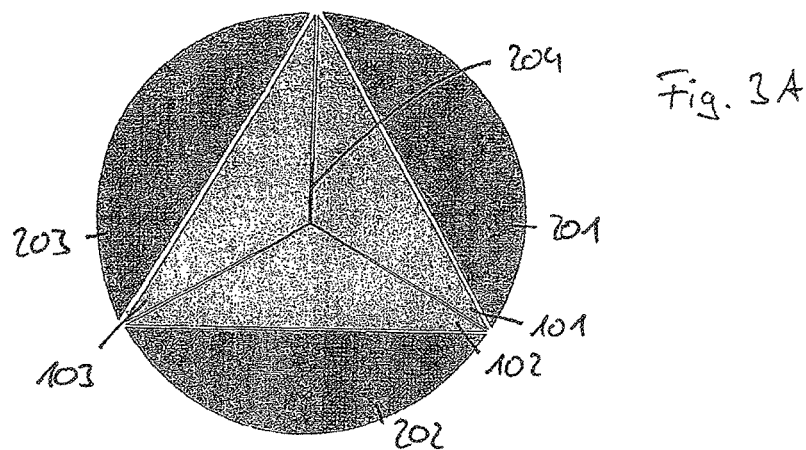
FIGS. 3A, 3B and 3C are schematic representations of a head of a medical gripping device according to a fifth embodiment in different states.

Hereinafter a first embodiment of the medical gripping device of the present invention is described with reference to the FIGS. 1, 2 and 6 to 11.

The medical gripping device (1) of the first embodiment includes a flexible shaft (2) having a front end (3) and a rear end (14). The shaft (2) is in the form of a resilient spiral exhibiting compressive strength. Moreover it includes a web (4) consisting of one single Web element mounted to the first end (3) of the shaft (2). Two branches (actuatable leg members 5,6) are rotatably hinged to the web (fixed leg member 4). Parts of two flexible control mechanisms (7, 151, 155; 8, 152, 156) are arranged in the shaft (2) and each individual branch (5, 6) is movable vis-à-vis the web (4) by means of a separate control mechanism (7, 151, 155; 8, 152, 156). In this case the branch (6) on the left in FIG. 1 is controllable by the control mechanism (8, 152, 156) and the branch (5) on the right in FIG. 1 is controllable by the control mechanism (7, 151, 155). In the first embodiment of the medical gripping device each of the control mechanisms (7, 151, 155; 8, 152, 156) has a transmission element (7, 8) exhibiting tensile and compressive strength which extend jointly in the shaft (2). Each of these transmission elements (7, 8) is connected to a branch (5, 6) at the front end (3) of the shaft (2). In addition, each of the control mechanisms (7, 151, 155; 8, 152, 156) includes a control device (151, 155; 152, 156) provided at the rear end (14) of the connecting element (160) and being connected to the pertinent transmission element (7, 8), wherein each transmission element (7, 8) transmits the movement output by the respective control device (151, 155; 152, 156) to the respective branch (5, 6).

In this embodiment the transmission elements (7, 8) are Bowden cables and the control devices (151, 155; 152, 156) consist of rails (151, 152) and slides (155, 156) including gripping elements (155G, 156G). The gripping elements (155G, 156G) are actuated in one direction to open the respective branch (5, 6) and are actuated in the opposite direction to close the respective branch (5, 6). In order to open the branches the slides are moved toward the shaft (2). The gripping elements (155G, 156G) are provided at a common handle (150).

The branches (5, 6) and/or the pertinent web element (4) are not distinguishable in this embodiment. However, in a medical gripping device (1) according to this embodiment even later grooves or engravings can be provided at the branches (5, 6) and/or the web element (4) and the pertinent gripping elements (155G, 156G) or slides (155, 156) so that then a definite association of the gripping element (155G, 156G) with the branch (5, 6) is possible. Since in this embodiment only one web element (4) is provided, the engraving or groove for distinction can be provided, for instance, at both side faces of the web element (4), wherein, for instance, a groove is provided at both side faces of the web element (4) in such manner that it is closer to the branch (5) and the gripping element (155G) pertaining to the branch (5) is equally provided with a groove.

The branches (5, 6) and the one web element (4) are arranged symmetrically. That is to say, the longitudinal axis of the one web element (4) is identical with the longitudinal axis of the medical gripping device (1) and the two branches (5, 6) are hinged to the web element (4) to be diametrally opposed. The branches (5, 6) are moreover rotatable in radial direction with respect to the axis of the gripping device (1).

As shown in FIGS. 1 and 2, the Bowden cables (7, 8) are mounted to extensions or levers (5', 6') of the branches (5, 6). These extensions or levers (5', 6') are designed such that they are provided in a recess of the web element (4) when the branches (5, 6) are closed. Thus the diameter of the head (18) of the gripping device (1) can be kept very small in the closed state. The head (18) of the gripping device (1) denotes the elements provided at the front end (3) of the gripping device (1).

The Bowden cables (7, 8) are mounted to the extensions (5', 6') of the branches (5, 6) by means of hinge mechanisms. The front end of the web element (4) is somewhat thickened and the front ends of the branches (5, 6) are slightly bent and tapered toward the web element (4) so that they engage in the front end of the web element (4) in which a respective recess is provided. The two branches (5, 6) are of equal size and are hinged at the same axis to the web element (4).

Figure 6:
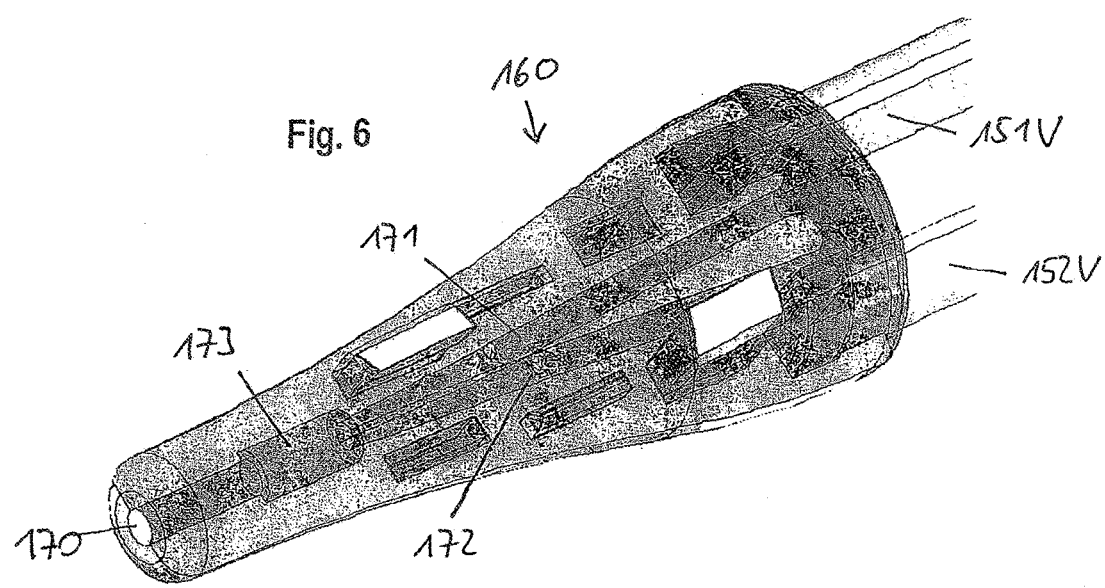
FIG. 6 is a perspective view of the connecting element in which part of the connecting element is shown as wire-frame model.
Figure 7:
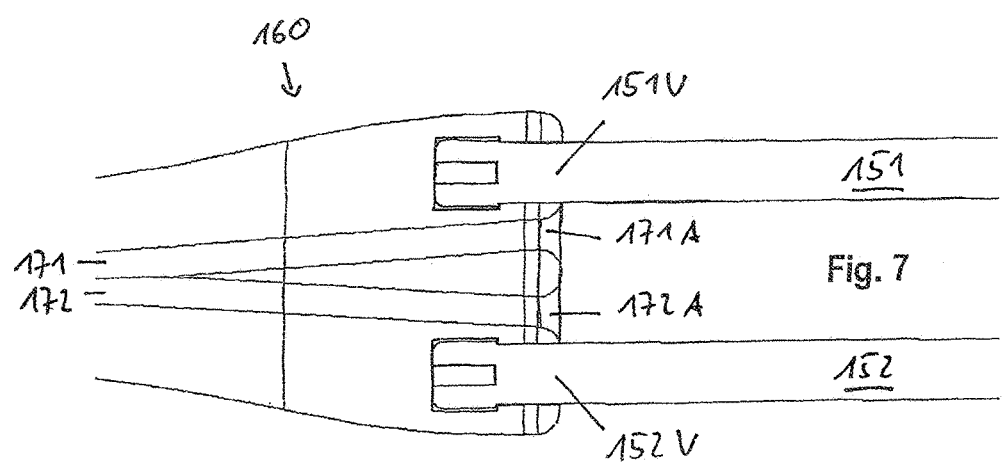
FIG. 7 is a lateral view of the rear area of the connecting element and of the front area of the handle.
Figure 9:
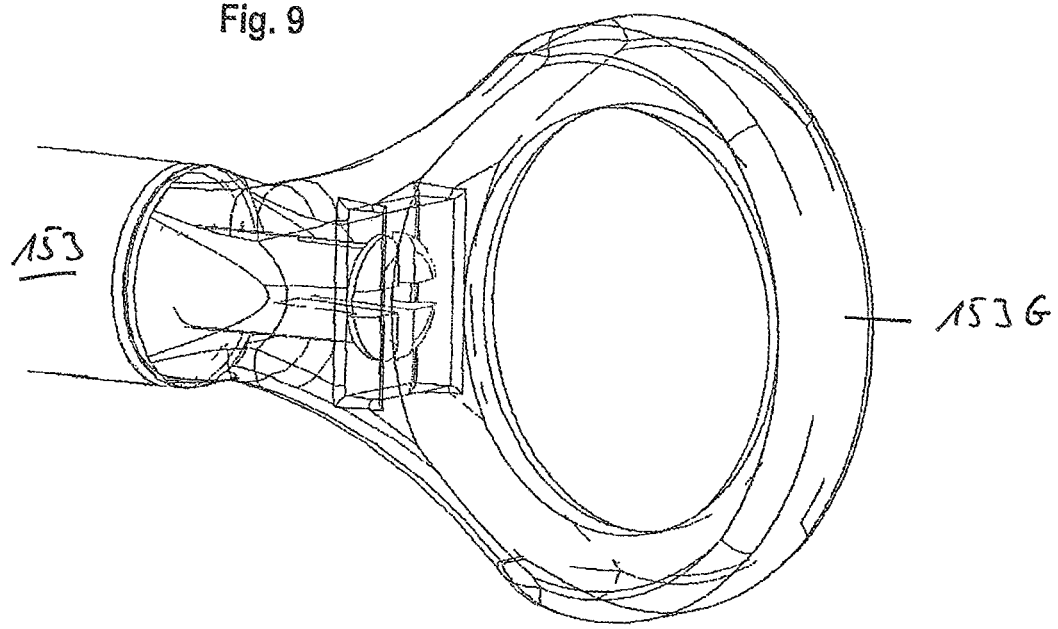
FIG. 9 is a perspective view of a rear end of the handle including gripping element.

At the rear end (14) of the shaft (2) in this embodiment a connecting element (160) is formed, as it is shown in FIGS. 6 and 7, to which the handle (150) is connected which substantially consists of the rails (151, 152), the connecting element (153), the slides (155, 156) and the gripping elements (155G, 156G, 153G). The handle (150) is shown especially in the FIGS. 8 and 10.

Through passages (170, 171, 172) are provided in the connecting element. More precisely, the through passage (170) is split in a chamber (173) into the two through passages (171, 172) which run apart in V-shape and guide a respective transmission element (7, 8) within them. The connecting element (160) consists of two parts likewise connected by a plug-in connection. The through holes (171, 172) are widened toward the handle (150), as this is clearly visible in FIG. 7. In this way a smooth insertion of the transmission elements (7, 8) into the respective through hole (171, 172) is possible when operating the respective branch (5, 6).

At the connecting element (160) the two rails (151, 152) are fixed with their front ends (151V, 152V) as this is shown especially in FIG. 7. Here the rails (151, 152) are caught with their front ends (151V, 152V) in the connecting element (160).

A slide (155, 156) is attached to each rail (151, 152) such that each slide (155, 156) encompasses the corresponding rail (151, 152). The two rails are connected to each other at their rear ends (151H, 152H) by a connecting portion (153), wherein a gripping element (155G, 156G, 153G) is provided in the form of a substantially circular eye at each slide (155, 156) (the gripping element 153G being slightly oval). In this embodiment the gripping elements (155G, 156G, 153G) are all provided in the same plane. The gripping element (153G) is fastened to the connecting portion (153) equally by a plug-in connection.

Figure 10:
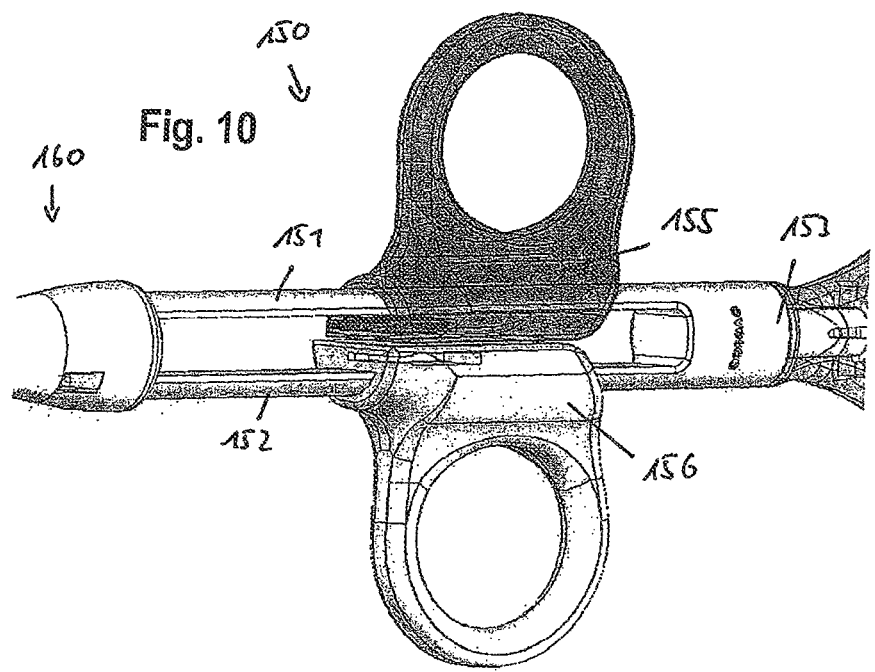
FIG. 10 is a perspective view of the handle.
Figure 11:
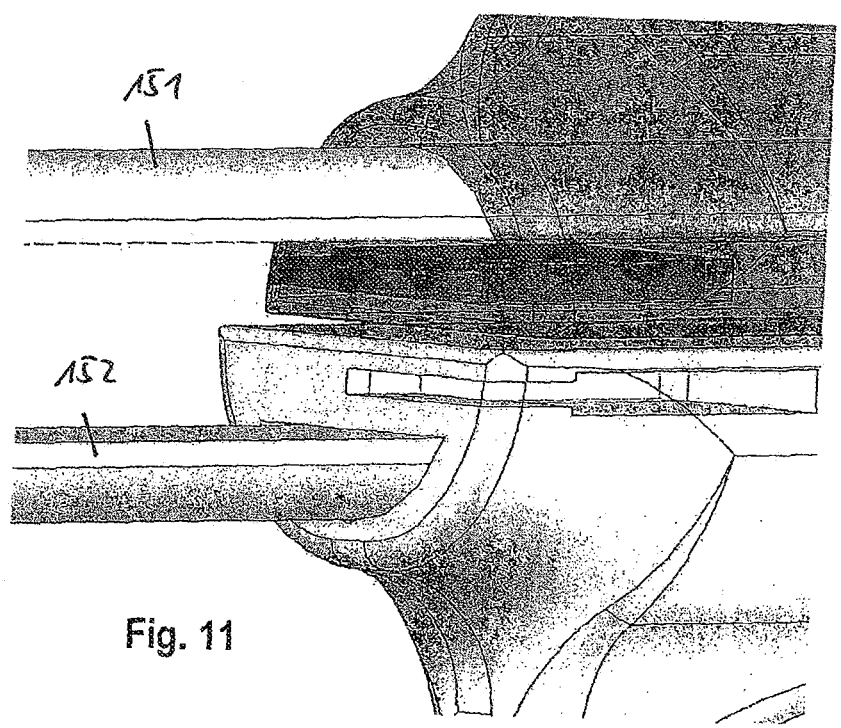
FIG. 11 is an enlarged view of a part of FIG. 10.

The transmission elements (7, 8) are connected to the slides (155, 156) in the area between the rails (151, 152). In FIG. 10 recesses are shown into which the transmission elements (7, 8) are inserted and are then fastened by means of undercuts. In FIG. 11 the transmission elements (7, 8) are not shown.

In this embodiment the entire handle is made of plastic material by injection molding. In addition, all connections are realized by plug-in connections, whereby the assembly of the handle (150) and the fastening of the transmission elements (7, 8) to the slides (155, 156) can be carried out without using any tools. The slides (155, 156) consist of two half-shells which can be clicked together in a way comparable to the connecting element (160), wherein they encompass the respective rail (151, 152). The shape of the rails (151, 152) and of the corresponding recesses in the slides (155, 156) prevents the gripping elements (155G, 156G) from laterally turning away during gripping. The click connection of the rear gripping element (153G), too, is designed such that the gripping element (153G) cannot twist.

The front opening of the through hole (170) is moreover in direct contact with the flexible shaft (2).

This embodiment is directed to a medical gripping device having two mouths. A similar design can also be employed, however, for medical gripping devices having three or more mouths. For this purpose merely an appropriate number of rails, slides, through holes in the connecting element and transmission elements have to be provided which advantageously have to be disposed symmetrically with respect to the central axis of the gripping device.

Second Embodiment

A second embodiment of the medical gripping device is described with reference to FIGS. 5A and 5B.

The medical gripping device (1) of the second embodiment also exhibits a flexible shaft (2) including a front end (3) and a rear end (14), a web (4) consisting of two web elements (4A, 4B), the web elements (4A, 4B) being mounted to the front end (3) of the shaft (2), two branches (5, 6) hinged to the web elements (4A, 4B) at the hinge points (51A, 61B) and two flexible control mechanisms (7, 151, 155; 8, 152, 156) which are arranged at least partially in the shaft (2). The branch (5) is rotatable vis-à-vis the web element (4A) by the control mechanism (7, 151, 155) and the branch (6) is rotatable vis-à-vis the web element (4B) by the control mechanism (8, 152, 156). In this embodiment the web (4) consists of two web elements (4A, 4B), with none of the web elements (4A, 4B) being rigidly mounted to the shaft. An element (70) is arranged at the web elements (4A, 4B) such that the web elements (4A, 4B) can be rotated about the hinge points (41A, 41B) relative to each other. The element (70) is an elastic element, viz. a compression spring in this case. The compression spring (70) forces the ends (42A, 42B) of the web elements (4A, 4B) which are distant from the body apart. If, however, as illustrated in FIG. 5B, the gripping device (1) is pulled somewhat into a working channel (80) of an endoscope, the web elements (4A, 4B) are pressed toward each other by the movement and the contact with the edge (81) of the working channel (80) and the compression spring (70) is also compressed. As in the case of the first embodiment, the control mechanisms (7, 151, 155; 8, 152, 156) have respective transmission elements (7, 8) exhibiting tensile and compressive strength which extend jointly in the shaft (2), each of these transmission elements (7, 8) being connected to a branch (5, 6) at the front end (3) of the shaft (2). More precisely, the transmission element (7) is hinged to the mounting point (52) at the lever (5') of the branch (5) and the transmission element (8) is hinged to the mounting point (62) at the lever (6') of the branch (6). Each transmission element (7, 8) transmits the movement output by the respective control device (7, 151, 155; 8, 152, 156) to the corresponding branch (5, 6).

In the second embodiment the transmission elements (7, 8) are Bowden cables. The gripping elements (155G, 156G) are identical as to their shape and function to the gripping elements (155G, 156G) of the first embodiment except for the fact that the gripping element (155G) includes a groove. Also in the second embodiment the gripping elements (155G, 156G) are provided at a handle (150).

The branches (5, 6) are distinguishable, wherein the branch (5) has a groove similar to that of the gripping element (155G) at its outside. Thus it is evident for the user which gripping element (155G, 156G) controls which branch (5, 6).

As it is illustrated in the FIGS. 5A and 5B, the branches (5, 6) and the web elements (4A, 4B) are arranged symmetrically and the branches (5, 6) are rotatable about the hinge points (51A, 61B) in radial direction with respect to the axis of the gripping device (1). The web elements (4A, 4B) are rotatable about the hinge points (41A, 41B) in radial direction with respect to the axis of the gripping device (1).

The gripping device (1) of the second embodiment is adapted to achieve the same effects as the gripping device (1) of the first embodiment. Moreover, by forming the web (4) of two web elements (4A, 4B) the distance of the two mouths of the gripping device (1) can be adjusted when the gripping device (1) is used together with an endoscope. Then the head (18) of the gripping device (1) of the second embodiment can be pulled into the working channel (80) of the endoscope so far that the web elements (4A, 4B) are adjacent to the front edge (81) of the working channel (80) of the endoscope and are compressed by this edge (81). Pulling the head (18) of the gripping device (1) into the working channel is achieved by pulling the shaft (2) of the gripping device (1) at the other end of the working channel (80).

Third Embodiment

Figure 3B:
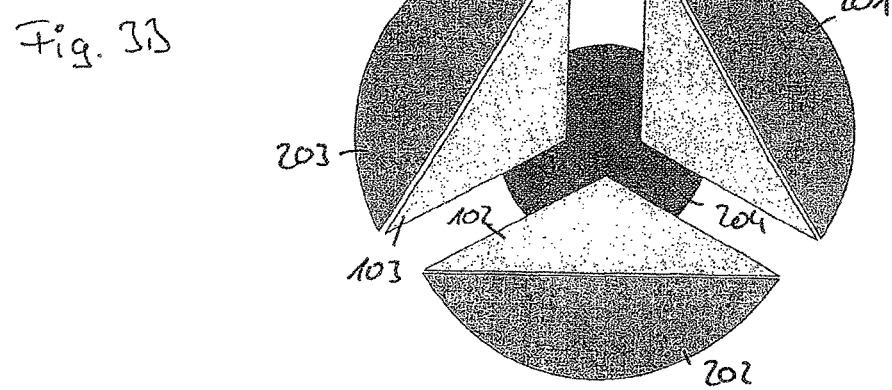
Figure 3C:
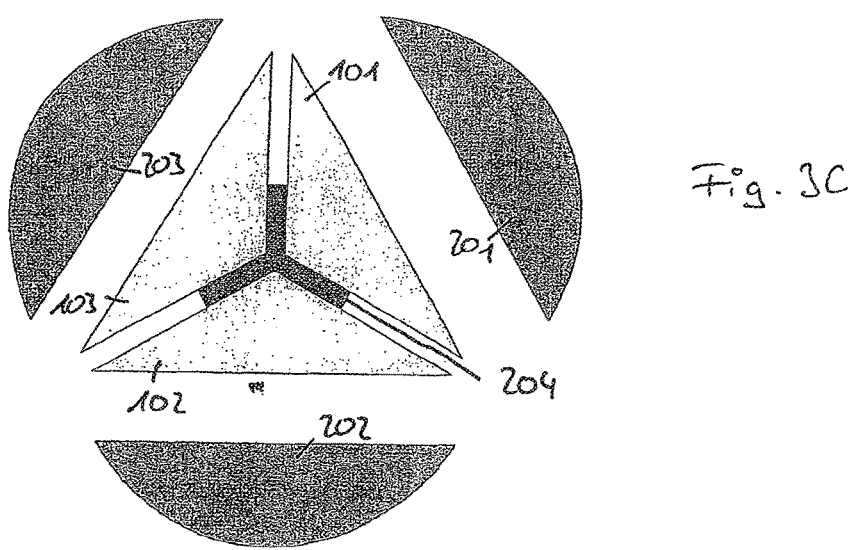
Figure 4A:
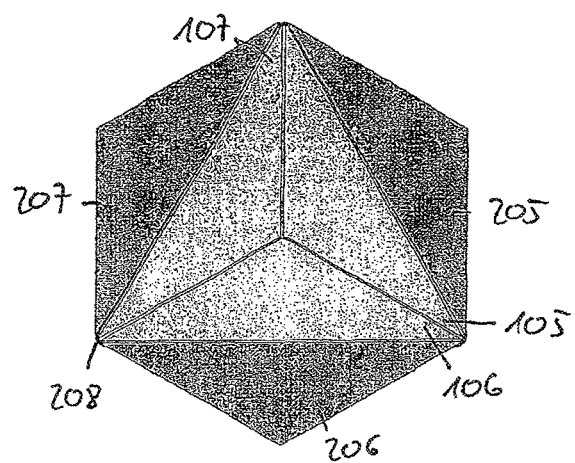
FIGS. 4A, 4B and 4C are schematic representations of a head of a medical gripping device according to a sixth embodiment in different states.
Figure 4B:
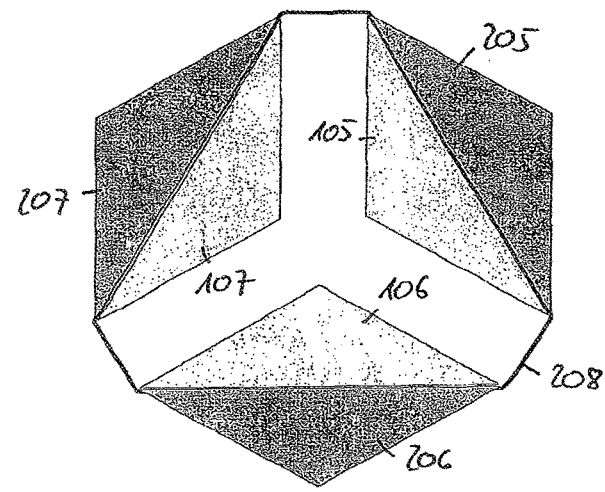
Figure 4C:
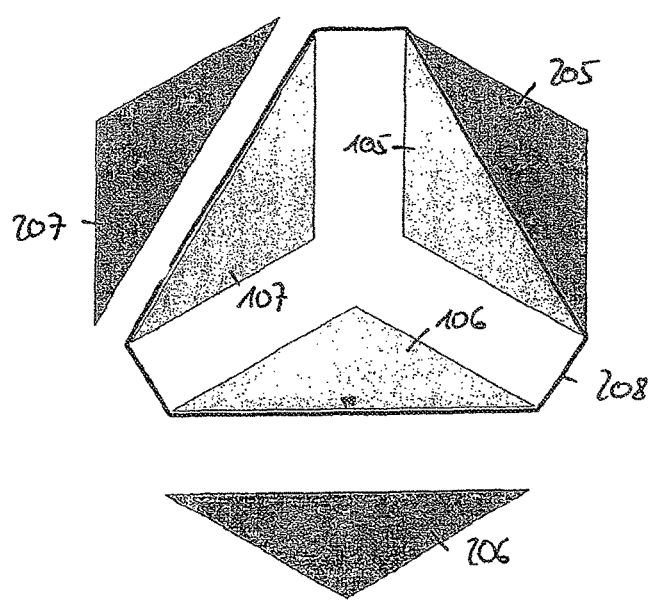

In the third embodiment of the gripping device (1) shown in FIGS. 4A to 4C the shape of the branches (205, 206, 207) differs from that of the FIGS. 3A to 3C. Furthermore, in this embodiment the web elements (105, 106, 107) are pulled together by a rubber strap (208). In this embodiment the web elements (105, 106, 107) are designed so that they include electromagnetic means which force the web elements (105, 106, 107) apart when they are activated. The strength of the magnetic repulsion can be adjusted via the supplied current. The rubber strap (208) has a predetermined elasticity. Therefore, via the set magnetic repulsion of the web elements (105, 106, 107) the distance of the web elements from each other can be adjusted. The transmission elements for the branches (205, 206, 207) of this embodiment are Bowden cables as in the preceding embodiments. The electric wires for the electromagnetic means are accommodated in this embodiment in the shell of the shaft (2) of the gripping device (1). The handle (150) of the gripping device (1) of this embodiment moreover includes a rotary element with the aid of which the electric current can be adjusted for the electromagnetic means.

Further Embodiments

In accordance with another embodiment, the branches (205, 206, 207) of the third embodiment can also be actuated by means of micro motors. The handle (150) can be configured, for instance, so that it includes three slides for controlling the opening of the branches and a rotary element for controlling the distance of the web elements (105, 106, 107). The slides are then in the form of linear potentiometers, for instance.

In accordance with another embodiment, also the distance of the web elements from each other can be adjusted by means of a Bowden cable.

In the case of mechanical transmission elements the slides (155, 156) can be biased toward the connecting element (160) also by springs so that when the slides are released (i.e. currently no operation takes place and no fixing means is provided) the slides are moved toward the connecting element (160) by the spring bias so that the corresponding branches (5, 6) are opened. The slides can also be biased in the opposite direction so that they can automatically be closed.

The gripping device (1) described in this description for medical purposes only can also be used in precision engineering, for instance.

The present invention discloses a medical gripping device (1) comprising a flexible shaft (2) having a front end (13) and a rear end (14). The device includes a web (4) consisting of at least one web element, the web (4) being mounted to the front end (3) of the shaft (2), at least two branches (5, 6) hinged at the web (4) and at least two flexible control mechanisms (7, 151, 155; 8, 152, 156) arranged at least partially in the shaft (2). Each single branch (5, 6) is individually movable vis-à-vis the web (4) by means of a separate control mechanism (7, 151, 155; 8, 152, 156). At the rear end (14) of the flexible shaft (2) a handle (150) is provided by which the medical gripping device (1) can be held and actuated.

The invention claimed is:

1. A medical gripping device, comprising:
a flexible shaft having a front end and a rear end;
a fixed leg member mounted at the front end of the shaft;
first and second actuatable leg members mounted at the front end of the shaft adjacent to the fixed leg member such that a mouth is formed between each actuatable leg member and the fixed leg member;
a handle comprising first and second slides;
a first at least partially flexible control mechanism arranged at least partially in the shaft, the first mechanism comprising the first slide and a first transmission element connecting the first slide to the first actuatable leg member;
a second at least partially flexible control mechanism arranged at least partially in the shaft, the second control mechanism comprising the second slide and a second transmission element connecting the second slide to the second actuatable leg member;
a connecting element connecting the handle to the rear end of the flexible shaft, the connecting element having a chamber which is split into first and second through passages which run apart in a V-shape and guide the first and second transmission elements with the first transmission being guided in the first through passage and the second transmission element being guided in the second through passage;
wherein the first and second control mechanisms are configured to independently operate the first and second actuatable leg members such that the medical gripping device includes two mouths adapted to be opened and closed independently of each other thus two tissue portions can be separated gripped and fixed.

2. The medical gripping device of claim 1, wherein the first and second through passages are widened toward the handle in order to permit a smooth insertion of the first and second transmission elements into the first and second through passages.

3. The medical gripping device of claim 1, wherein the first and second transmission elements are combined into the chamber at the split.

4. The medical gripping device of claim 1, wherein the first and second through passages have openings in an area proximate to the handle which are arranged rotationally symmetrical about an axis of the connecting element in a plane perpendicular to the axis on an orbit.

5. The medical gripping device of claim 4, wherein the openings are evenly spaced on the orbit.

6. The medical gripping device of claim 1, wherein the first and second transmission elements are Bowden cables.

* * * * *